United States Patent
Goeppert

(10) Patent No.: US 8,908,192 B2
(45) Date of Patent: Dec. 9, 2014

(54) METHOD AND APPARATUS FOR QUALIFYING OPTICS OF A PROJECTION EXPOSURE TOOL FOR MICROLITHOGRAPHY

(71) Applicant: Carl Zeiss SMT GmbH, Oberkochen (DE)

(72) Inventor: Markus Goeppert, Karlsruhe (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 0 days.

(21) Appl. No.: 13/754,446

(22) Filed: Jan. 30, 2013

(65) Prior Publication Data

US 2013/0148105 A1 Jun. 13, 2013

Related U.S. Application Data

(63) Continuation of application No. PCT/EP2011/003681, filed on Jul. 22, 2011.

(60) Provisional application No. 61/369,225, filed on Jul. 30, 2010.

(30) Foreign Application Priority Data

Jul. 30, 2010 (DE) .......................... 10 2010 038 697

(51) Int. Cl.
*G01B 9/02* (2006.01)
*G03F 7/20* (2006.01)
*G01N 21/95* (2006.01)

(52) U.S. Cl.
CPC ............ *G01N 21/95* (2013.01); *G03F 7/70591* (2013.01); *G03F 7/70941* (2013.01); *G03F 7/706* (2013.01); *G03F 7/7085* (2013.01)
USPC .......................................... 356/521; 356/520

(58) Field of Classification Search
USPC .......................................... 356/520
See application file for complete search history.

(56) References Cited

U.S. PATENT DOCUMENTS

| 5,032,734 | A | 7/1991 | Orazio, Jr. et al. |
| 6,344,898 | B1 | 2/2002 | Gemma et al. |

(Continued)

FOREIGN PATENT DOCUMENTS

| DE | 10109929 A1 | 11/2001 |
| DE | 10360581 A1 | 7/2005 |

(Continued)

OTHER PUBLICATIONS

A. Barty et al., : "Multilayer defects nucleated by substrate pits: a comparison of actinic inspection and non-actinic inspection techniques", Proceedings of SPIE, vol. 6349, Jan. 1, 2006, pp. 63492M-63492M-9.
J. Kirk, et al., : "Pinholes and pupil fills", Microlithography World, Autumn 1997, pp. 25-27 and 34.

*Primary Examiner* — Tarifur Chowdhury
*Assistant Examiner* — Jonathon Cook
(74) *Attorney, Agent, or Firm* — Edell, Shapiro & Finnan, LLC

(57) ABSTRACT

A method for qualifying optics (16; 14, 16) of a projection exposure tool (10) for microlithography. The optics include (16; 14, 16) at least one mirror element (14-1 to 14-7, 16-1 to 16-6) with a reflective coating (52) disposed on the latter. The method includes: irradiating electromagnetic radiation (13, 42) of at least two different wavelengths onto the optics (16; 14, 16), a penetration depth of the radiation into the coating (52) of the mirror element varying between the individual wavelengths, taking an optical measurement on the optics (16; 14, 16) for each of the wavelengths, and evaluating the measurement results for the different wavelengths taking into consideration a respective penetration depth of the radiation into the coating (52) of the mirror element for each of the different wavelengths.

11 Claims, 7 Drawing Sheets

(56) References Cited

U.S. PATENT DOCUMENTS

| | | |
|---|---|---|
| 7,333,216 B2 | 2/2008 | Wegmann et al. |
| 7,538,856 B2 | 5/2009 | Kajiyama et al. |
| 2002/0041368 A1 | 4/2002 | Ota et al. |
| 2005/0264779 A1 | 12/2005 | Hasegawa et al. |
| 2006/0187435 A1* | 8/2006 | Ohsaki .......................... 355/55 |
| 2008/0144043 A1 | 6/2008 | Wegmann et al. |
| 2009/0002663 A1 | 1/2009 | Freimann et al. |

FOREIGN PATENT DOCUMENTS

| | | |
|---|---|---|
| DE | 102005056914 A1 | 5/2007 |
| EP | 1452851 A1 | 9/2004 |
| WO | 2009089999 A1 | 7/2009 |

\* cited by examiner

METHOD AND APPARATUS FOR QUALIFYING OPTICS OF A PROJECTION EXPOSURE TOOL FOR MICROLITHOGRAPHY

This application is a Continuation of PCT/EP2011/003681, with an international filing date of Jul. 22, 2011, and which claims priority to German Patent Application No. 10 2010 038 697.9 filed Jul. 30, 2010 and to U.S. Provisional Application No. 61/369,225 filed Jul. 30, 2010. The entire disclosures of each of these three prior applications are incorporated into the present application by reference.

FIELD OF AND BACKGROUND TO THE INVENTION

The invention relates to a method and an apparatus for qualifying optics of a projection exposure tool for microlithography, and to a projection exposure tool comprising this type of apparatus. Furthermore, the invention relates to a sensor module for interferometric wavefront measurement on optics of a projection exposure tool for microlithography.

This type of projection exposure tool has different optics modules, including an illumination system for illuminating a mask with exposure radiation and a projection objective for imaging object structures of the mask onto a substrate in the form of a wafer. Depending on the exposure wavelength, the optics modules have different numbers of mirror elements. When using EUV radiation with a wavelength of e.g. 13.5 nm, mirror elements are used for all of the optical elements of the exposure optical path. The mirror elements optimised for the reflection of EUV radiation have a coating which generally consists of a multilayer structure. The EUV radiation penetrates deeply into the multilayer structure, parts of the EUV radiation being reflected on each individual layer.

Before placing in operation the projection exposure tool and regularly during operation it is necessary to qualify the optical properties of the individual optics modules. The imaging properties of the projection exposure tool often deteriorate during operation of the tool. There can be many causes for this, for example there can be degradation of the mirrors, misalignment of the mirrors etc. The problem then often arises that the cause of such deterioration can not be isolated reliably.

OBJECTS AND SUMMARY OF THE INVENTION

It is an object of the invention to provide a method as well as an apparatus and a projection exposure tool with which the aforementioned problems can be resolved, and in particular the cause of defective imaging behaviour of a projection exposure tool with at least one mirror can be located.

The aforementioned object is achieved according to a first formulation of the invention, for example, with a method for qualifying optics of a projection exposure tool for microlithography, the optics comprising at least one mirror element with a reflective coating disposed on the latter. The method according to the invention comprises the following steps: irradiating electromagnetic radiation of at least two different wavelengths onto the optics, a penetration depth of the radiation into the coating of the mirror element varying between the individual wavelengths, taking an optical measurement on the optics for each of the wavelengths, and evaluating the measurement results for the different wavelengths taking into account a respective penetration depth of the radiation into the coating of the mirror element for each of the different wavelengths.

In other words, according to the invention a first electromagnetic radiation and a second electromagnetic radiation is irradiated onto the optics to be examined. The first and the second radiation have different wavelengths, in particular different average wavelengths, such that the penetration depth of the first radiation differs from the penetration depth of the second radiation into the coating of the mirror element. The two radiations can have narrowband or also broadband wavelength ranges. In the case of broadband wavelength ranges the latter can also overlap. It is essential that the wavelength ranges are not identical, and so different penetration depths are produced. Preferably, the penetration depth differs between the two radiations by at least 2%, in particular by at least 5% or at least 50% of the thickness of the coating. In absolute values it is advantageous if the penetration depth varies between the wavelengths by at least 10 nm, preferably by at least 50 nm. For example, the first radiation can be EUV radiation, and the second radiation a radiation in the DUV wavelength range, such as for example 193 nm or 248 nm radiation.

According to the invention, both with the first radiation and with the second radiation an optical measurement is taken on the optics to be examined. This type of optical measurement can comprise e.g. a wavefront measurement by shearing interferometry, a pupil transmission measurement and/or the measurement of the location of an image position in the substrate plane when imaging an object structure. Since the penetration depths into the coating of the radiations forming the basis of the individual optical measurements vary due to the different wavelengths, it is to be expected that the measurement results also differ. For example, a lateral image offset between the images of a specific object structure is typically observed using different wavelengths.

According to the invention the measurement results for the different wavelengths are evaluated, during the evaluation the respective penetration depth for each of the different wavelengths being taken into consideration. If one determines, for example, a deviation in the lateral image offset in relation to the anticipated image offset or in relation to an image offset measured at an earlier time, this suggests degradation of the optics. Since, however, the respective penetration depth of the radiation into the coating of the optics is known for the individual wavelengths, by taking into consideration, according to the invention, the penetration depths, the layer depth in which there is degradation can be narrowed down. The evaluation according to the invention thus makes it possible, for example, to locate any degradation of a specific individual layer of the multilayer coating. Furthermore, for example, any contamination present on the mirror surface can also be detected. Such contamination manifests itself, for example, by radiation with a visible wavelength being strongly absorbed by the latter, whereas for example EUV radiation is absorbed to a lesser degree. The measurement results of the optical measurement for the different wavelengths are therefore changed in a characteristic way.

The qualifying method according to the invention thus makes it possible to locate the cause for defective imaging behaviour of a projection exposure tool depending on the layer depth, i.e. e.g. degradation of individual layers or also mirror contaminations can be located. The method according to the invention further makes it possible, for example, to make a manipulator adjustment using optical measurements with wavelengths of greater than 100 nm. Thus, for example, an EUV objective can be qualified without the use of EUV radiation, and a possible result of this is saving of time when qualifying the projection exposure tool.

As already mentioned above, in one embodiment according to the invention, when evaluating the measurement results a layer depth-dependent deviation of an optical property of the coating of the at least one mirror from the desired state of the latter is determined. As optical properties of the coating with regard to which a layer depth dependent deviation can be determined, reflectivity, layer planarity and the absorption level of the coating can be considered.

In a further embodiment according to the invention the coating is configured as a multilayer structure, and when evaluating the measurement results the extent of a possible surface deformation of individual layers of the multilayer structure is determined. In other words, a possible degradation of individual layers of the multilayer structure, which can also be called a stack of layers or "multilayer" film, can be determined.

In a further embodiment according to the invention, as already mentioned above, when evaluating the optical measurement results the extent of a possible contamination of the coating is determined. For this purpose, one of the wavelengths is preferably chosen such that the radiation of this wavelength does not penetrate through the contamination, or only does so slightly, i.e. is absorbed or reflected by the contamination.

In a further embodiment according to the invention the optical measurement and the evaluation of the measurement results are repeated a number of times at intervals of time, and the state of the optics is monitored by comparing the evaluation results. Therefore, in this embodiment the qualification method is a method for monitoring the state of the optics over time.

In a further embodiment according to the invention the optical measurement on the optics comprises a wavefront measurement. This type of wavefront measurement can be taken, in particular, using an interferometric measurement, polarised or non-polarised, possibly using a shearing interferometer.

In a further embodiment according to the invention the optical measurement on the optics comprises a pupil transmission measurement. More details on the implementation of such a measurement are described below. With a pupil transmission measurement the intensity distribution of the exposure radiation passing into the mask plane can be analysed as a function of the angle. A pupil transmission measurement thus enables qualification of the illumination system. In particular with EUV lithography systems, due to the high intensities, problems often occur in the illumination system with regard to radiation-induced degradations and contamination of the mirror coatings.

As likewise already mentioned, in a further embodiment according to the invention, when taking the optical measurement on the optics a lateral offset between images of an object structure, which are generated as a result of the different wavelengths, is determined. A lateral offset is understood to be a displacement of the image of the object structure in the plane of the image, i.e. the substrate plane of the projection exposure tool.

In a further embodiment according to the invention one of the different wavelengths is the exposure wavelength of the projection exposure tool. According to one variant, the optics are configured as EUV optics, i.e. are designed to guide radiation in the EUV wavelength range. Advantageously, at least one of the different wavelengths is longer than 100 nm, and can e.g. be in the DUV-, in the visible or in the infrared wavelength range.

In a further embodiment according to the invention the optics to be qualified comprise a projection objective of the projection exposure tool. A projection objective is configured to image the structures of a lithography mask onto a substrate in the form of a wafer.

In a further embodiment according to the invention the optics to be qualified comprise illumination optics of the projection exposure tool. Illumination optics condition the radiation generated by a radiation source of the projection exposure tool as regards homogeneity and desired angle distribution, and directs the radiation conditioned in this way onto the lithography mask.

In a further embodiment according to the invention the optics comprise a number of mirror elements, and the cause for a deviation of an optical property of the optics from the desired property of the latter determined when evaluating the measurement results is assigned to one or to a number of mirror elements through ray tracing. In other words, the cause of the deviation with regard to the mirror element responsible for this is located by resorting to what is known to the person skilled in the art as "ray tracing" by simulation on the computer. Preferably the location of the cause on the mirror element is furthermore determined through ray tracing.

In a further embodiment according to the invention the optical measurement is a spectrometric measurement. With this type of measurement one can come to a conclusion regarding the type of contamination upon the basis of vibrational excitation, and this is with in-depth resolution upon the basis of the use of different wavelengths according to the invention.

The aforementioned object can be further achieved according to another formulation of the invention with an apparatus for qualifying optics of a projection exposure tool for microlithography wherein the optics comprise at least one mirror element with a reflective coating disposed on the latter, and the apparatus comprises: a measuring radiation source for generating electromagnetic radiation of at least one first wavelength different from an exposure wavelength of the projection exposure tool, a measuring device which is configured to take an optical measurement on the optics using the electromagnetic radiation of the first wavelength and of a further wavelength, and an evaluation device which is configured to evaluate the measurement results of the measuring device for the different wavelengths taking into account a respective penetration depth of the radiation into the coating of the mirror element for each of the different wavelengths. The further wavelength is preferably chosen such that the penetration depth of the radiation of the further wavelength deviates from the penetration depth of the radiation of the first wavelength. With regard to advantages which can be achieved with the apparatus according to the invention and further embodiments, reference is made to the above comments with regard to the qualifying method according to the invention.

Furthermore, according to a further aspect of the invention, a projection exposure tool for microlithography is provided which comprises the apparatus according to the invention for qualifying optics. The projection exposure tool is configured to image an object structure with exposure radiation onto a substrate, the electromagnetic radiation with the further wavelength being the exposure radiation. According to one embodiment the projection exposure tool is configured to operate with EUV radiation.

Furthermore, according to yet another aspect of the invention, a sensor module for an interferometric wavefront measurement on optics of a projection exposure tool for microlithography is provided. The sensor module according to the invention comprises: a locally resolving detector which is configured to detect electromagnetic radiation of at least two different wavelengths, and at least two diffraction gratings with different grating periods, the grating periods being adapted to diffract the electromagnetic radiation of respectively one of the different wavelengths. Using this type of sensor module, a wavefront measurement can be taken on an optical system of the projection exposure tool with radiation of two different wavelengths according to the qualifying method according to the invention described above. According to one embodiment one of the diffraction gratings is configured to diffract EUV radiation, and a second of the diffraction gratings to diffract radiation with a wavelength of greater than 100 nm. According to one variant according to the invention the sensor module according to the invention is part of the qualification apparatus according to the invention.

Moreover, according to the invention a projection objective is provided which is configured for use in an EUV projection exposure tool for microlithography. The projection objective comprises: mirror elements which define an optical path through the projection objective, an apparatus for observing the surface cleanliness of a last mirror element in the optical path, and a fault elimination apparatus for cleaning or exchanging the last mirror element. The last mirror element is the mirror element in the optical path of the projection objective which during operation of the projection exposure tool is closest to the wafer.

According to one embodiment according to the invention, the qualifying apparatus according to the invention described above is used as the apparatus for observing the surface cleanliness.

According to a further embodiment according to the invention the apparatus for observing the surface cleanliness comprises an interferometer arrangement for measuring the last mirror element. Here the interferometer arrangement comprises a measuring radiation source, beam forming optics, a back-reflector and a two-dimensionally locally resolving radiation detector. The latter are arranged outside of the optical path through the projection objective, and are configured such that: measuring radiation emitted by the measuring radiation source strikes a first expanded region of an optical surface of the last mirror element through the beam-forming optics as an expanded bundle of rays, after a first interaction with the last mirror element measuring radiation striking the optical surface strikes the back-reflector as an expanded bundle of rays, measuring radiation reflected at the back-reflector strikes a second expanded region of an optical surface of the last mirror element, measuring radiation striking the second expanded region of the optical surface enters after a second interaction with the last mirror element into the beam-forming optics as an expanded bundle of rays, and the measuring radiation entering into the beam-forming optics strikes the two-dimensionally locally resolving detector in superposition with reference radiation. The second expanded region can be identical to the first expanded region, but can, however, also be different from the latter. The basic principle of the interferometer arrangement described above is known to the person skilled in the art from DE 10 2005 056 914 A1. Alternatively, the interferometer arrangement can also be used in other embodiments described in DE 10 2005 056 914 A1 in the projection objective according to the invention. These embodiments are herewith explicitly incorporated into the disclosure of this application.

In a further embodiment according to the invention the fault elimination apparatus is in the form of a cleaning apparatus for cleaning the last mirror element with atomic hydrogen.

The features specified with regard to the embodiments of the method according to the invention mentioned above can be applied correspondingly to the apparatus according to the invention. Conversely, the features specified with regard to the embodiments of the apparatus according to the invention mentioned above can correspondingly be applied to the method according to the invention.

BRIEF DESCRIPTION OF THE DRAWINGS

The above and further advantageous features of the invention are illustrated in the following detailed description of exemplary embodiments according to the invention with reference to the attached diagrammatic drawings. These show as follows:

FIG. 2 the projection exposure tool according to FIG. 1 in the region of the projection objective in an enlarged illustration in which, in addition to an exposure optical path, a measuring optical path is drawn in;

DETAILED DESCRIPTION OF EXEMPLARY EMBODIMENTS

In the exemplary embodiments described below elements which are similar to one another functionally or structurally are provided as far as possible with the same or similar reference numbers. Therefore, in order to understand the features of the individual elements of a specific exemplary embodiment reference should be made to the description of other exemplary embodiments or to the general description of the invention.

Figure 1:
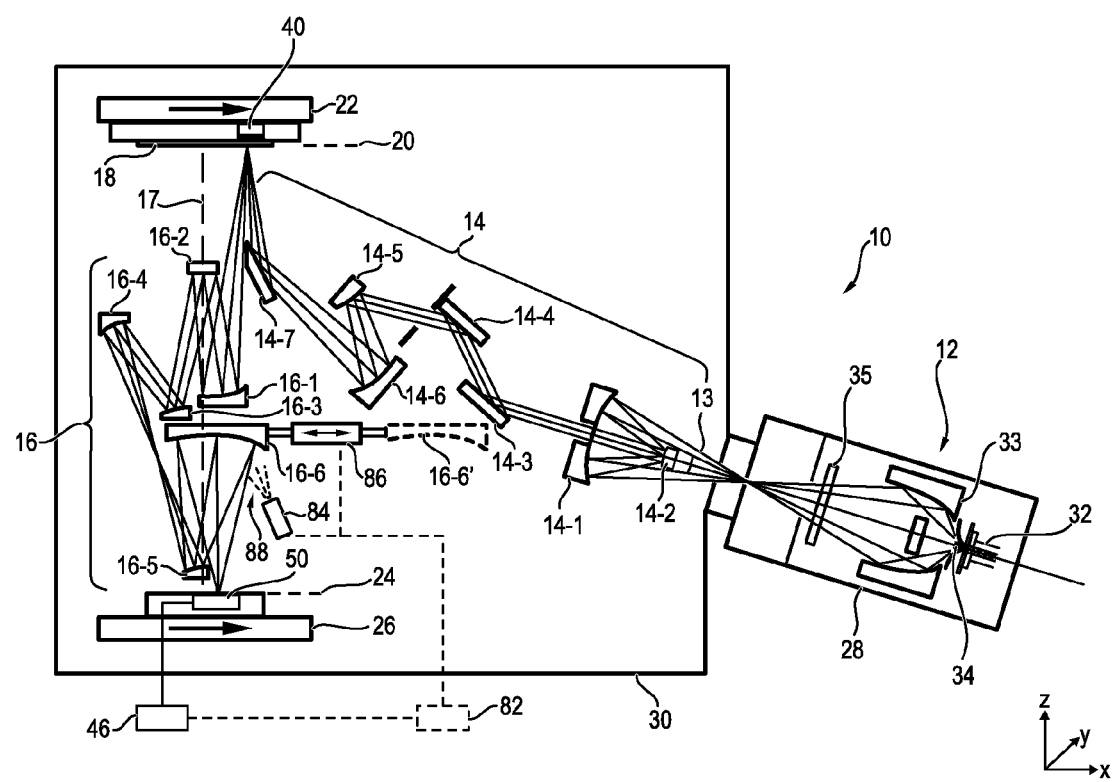
FIG. 1 a diagrammatic sectional view of a projection exposure tool for lithography comprising an apparatus integrated into the latter for qualifying the projection objective.

In order to facilitate the description of the projection exposure tool a Cartesian xyz coordinate system is specified in the drawing from which the respective relative position of the components shown in the figures can be taken. In FIG. 1 the x direction extends to the right, the y direction perpendicular to the plane of the drawing into the latter, and the z direction to the top.

FIG. 1 shows an exemplary embodiment of a projection exposure tool 10 for microlithography which is designed for operation in the EUV wavelength range. For this purpose the projection exposure tool 10 comprises an EUV radiation source 12 for generating electromagnetic radiation with a wavelength smaller than 100 nm, in the present case with a wavelength of 13.5 nm. The projection exposure tool 10 further comprises an illumination system 14 with which the radiation generated by the radiation source 12, which is referred to in the following as exposure radiation 13, is directed onto a mask 18 held by a mask table 22.

The exposure radiation 13 then passes through a projection objective 16 which is configured to image object structures on the mask 18 into a substrate plane 24. For this purpose a substrate in the form of a wafer (not shown in FIG. 1) is arranged on a substrate table 26 in the substrate plane 24. The projection exposure tool 10 can be in the form of a so-called scanner with which when imaging a product mask onto a substrate both the mask and the substrate table 26 are moved synchronously at different speeds in the x direction. Both the components of the radiation source 12 and the remaining components of the projection exposure tool 10 including the illumination system 14 and the projection objective 16 are surrounded by a vacuum container 28 and 30.

The EUV radiation source 12 comprises a discharging device 32, a plasma-emitter 34, a collector mirror 33 and a wavelength filter 35. The collector mirror 33 is formed, for example, by a spherical mirror which essentially collects EUV radiation radiated isotropically by the plasma emitter 34. The wavelength filter 35 retains undesired wavelength portions. Of course, as an alternative to the plasma discharging source shown in FIG. 1, other EUV radiation sources can be used. The radiation spectrum emitted by the plasma emitter 34 also comprises the DUV wavelength range (e.g. 193 nm or 248 nm). Therefore, with a corresponding configuration of the wavelength filter 35 the radiation source according to FIG. 1 can also be used as a DUV source. In a further embodiment one dispenses entirely with a wavelength filter. Depending on the measuring wavelength desired, structures of a corresponding size are illuminated on the mask 18, and the measurements are evaluated using a lock-in technique.

In the embodiment shown the illumination system 14 comprises seven mirrors 14-1 to 14-7 which are configured to direct the exposure radiation 13 generated by the radiation source 12 in the desired angle distribution onto the mask 18. The exposure radiation 13 is reflected on the surface of the mask 18 and then passes through the projection objective 16 which, in the present embodiment, comprises six mirror elements 16-1 to 16-6. The projection objective 16 has an optical axis 17 which extends in the z direction.

Figure 2:
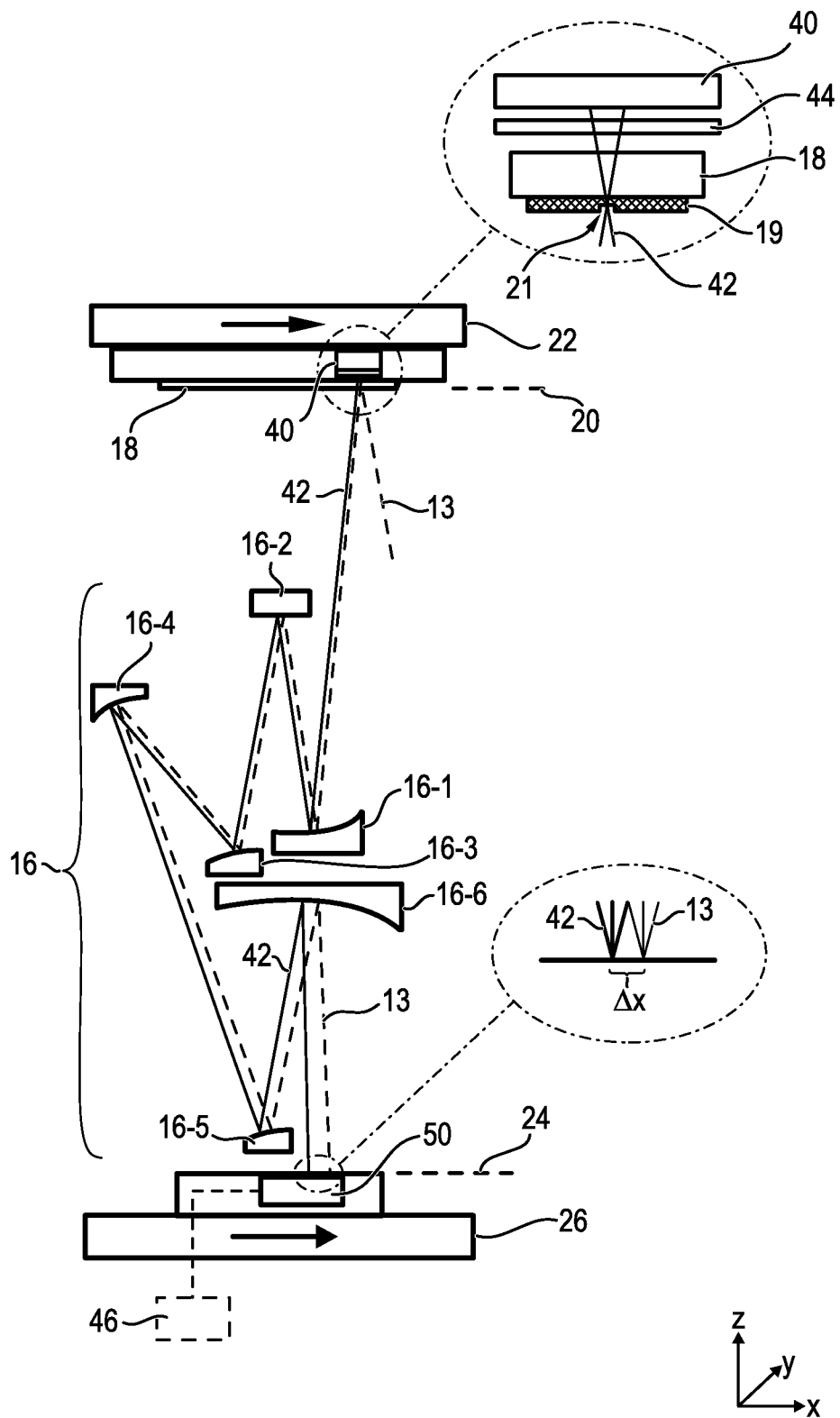

According to the invention an apparatus for qualifying the projection objective 16 is integrated into the projection exposure tool 10 according to FIG. 1. The apparatus comprises a measuring radiation source 40 and a sensor module 50. FIG. 2 illustrates a part of the projection exposure tool 10 comprising the mask table 22, the substrate table 26 and the projection objective 16, once again in an enlarged illustration. The optical path of the EUV exposure radiation 13 is drawn in here with broken lines. Moreover, an optical path of a measuring radiation 42 emitted by the measuring radiation source 40 is shown.

The measuring radiation 42 has a wavelength different from the wavelength of the EUV radiation. Preferably, the wavelength of the measuring radiation 42 is in the DUV, in the visible or in the infrared wavelength range, as explained in more detail below. The measuring radiation source 40 can include an LED, a laser diode, a laser or any other appropriate radiation source. The measuring radiation source 40 is integrated into the mask table 22, in particular into the mask holder, such that the measuring radiation 42 strikes the rear side of the mask 18 facing away from the projection objective 16. There can be positioned between the measuring radiation source 40 and the mask 18 an optical intermediate element 44, for example in the form of a diffusion disc, a diffusing screen or imaging optics, as shown in the detailed view of FIG. 2. In the exemplary embodiment shown in FIG. 2 the mask 18 has an arrangement of hole structures 21 in the form of pin holes in a layer 19 which is otherwise impermeable to radiation. The hole structures 21, of which only one is shown in FIG. 2 for the sake of simplicity, are imaged into the substrate plane 24 by the projection objective 16. Located here is the sensor module 50 for detecting the radiation passing into the substrate plane 24 and which is integrated into the substrate table 26.

According to the invention the projection objective 16 has electromagnetic radiation with two different wavelengths radiated through it, and for each of the wavelengths an optical measurement is taken. In the embodiment shown in FIG. 2 the radiation with the first wavelength is the exposure radiation 13 in the EUV wavelength range. The radiation with the second wavelength is the measuring radiation 42 generated by the measuring radiation source 40, e.g. in the visible wavelength range. Alternatively or in addition, the measuring radiation source 40 can also provide radiation with two different wavelengths, and the optical measurement can be taken upon the basis of this.

In a first variant of an optical measurement one measures the lateral image offset which, when imaging an object structure, passes out of the mask plane 20 into the substrate plane 24 between the two wavelengths used. In the embodiment according to FIG. 2 the hole structure 21 in the mask 18 serves as an object structure when imaging with the measuring radiation 42. For imaging with the exposure radiation 13 an analogous reflecting point structure in a non-reflective mask environment can be used. As shown by the detailed illustration of FIG. 2, for the different wavelengths a lateral image offset of $\Delta x$ occurs. The cause for this image offset is due to the fact that the electromagnetic radiation penetrates by different depths into a reflective coating 52 disposed over the mirrors 16-1 to 16-6 depending on the wavelength. This leads to a slight displacement occurring between the optical paths of different wavelengths with every mirror reflection.

Figure 3:
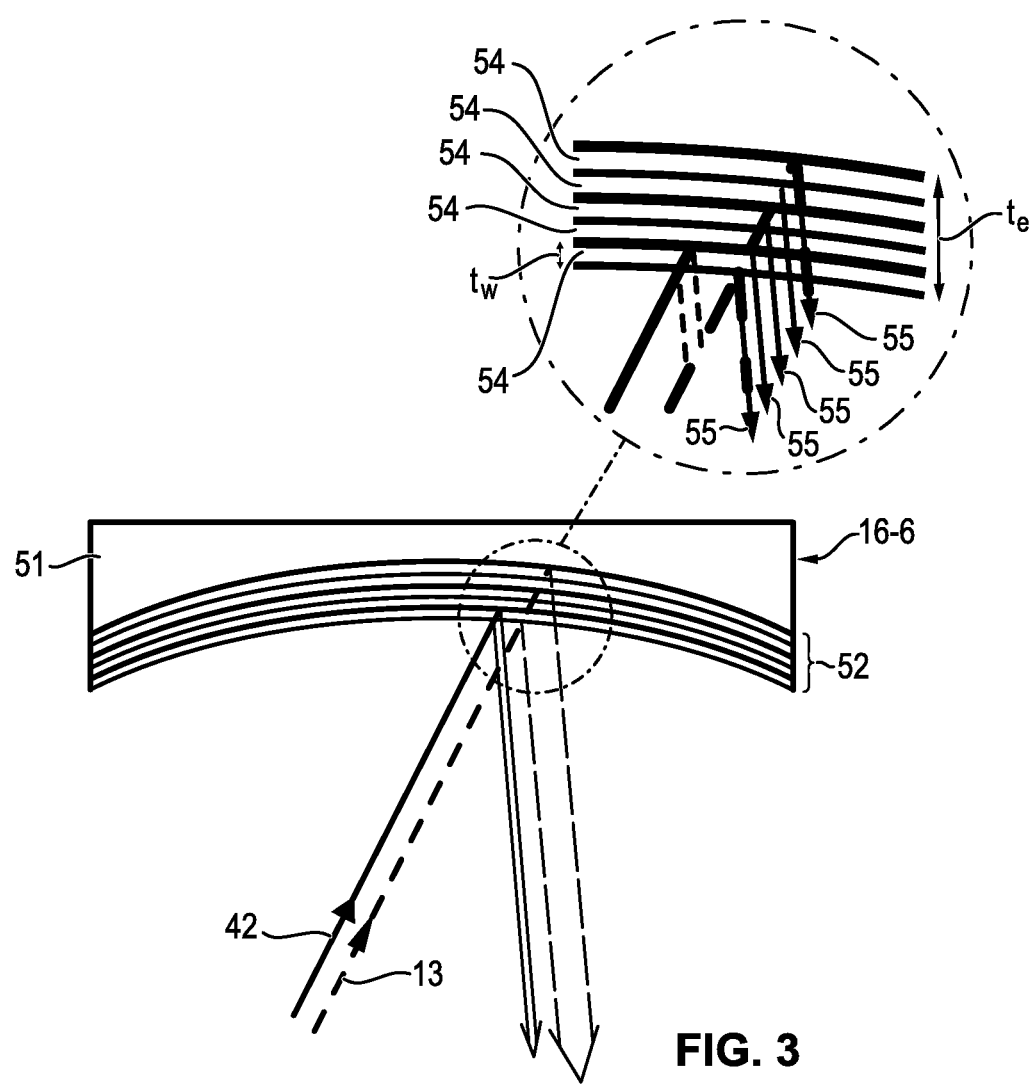
FIG. 3 an enlarged illustration of a mirror of the projection objective according to FIG. 2 showing different penetration depths of the irradiated radiation into a coating of the mirror.

FIG. 3 is a detailed view illustrating the reflection of the EUV exposure radiation 13 and the measuring radiation 42 on one of the mirrors of the projection objective 16, in the current case the mirror 16-6. The mirror comprises a mirror substrate 51 with a concave surface on which the coating 52 is disposed in the form of a multilayer structure. According to one embodiment the multilayer structure has molybdenum and silicon layers, and is designed to reflect EUV radiation.

Figure 4:
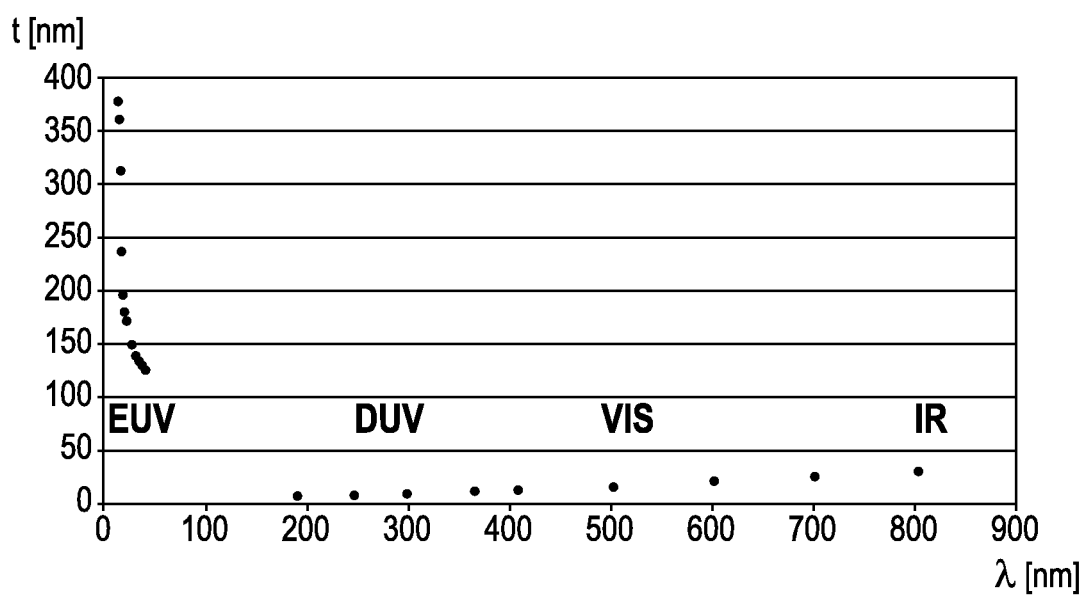
FIG. 4 a diagram which illustrates the penetration depths into the coating according to FIG. 3 for electromagnetic radiation of different wavelengths.

FIG. 4 shows a diagram in which the penetration depth t of irradiated radiation into the coating 52 dependent upon the wavelength of the radiation is illustrated. It is clear from this that EUV radiation penetrates substantially more deeply into the coating 52 than radiation with a wavelength of more than 100 nm. Furthermore, it is clear from the diagram that in the range over 100 nm the penetration depth increases again somewhat as the wavelength increases. Therefore, in the near infrared wavelength range (IR) the penetration depth is greater than in the visible wavelength range (VIS), which in turn exceeds the penetration depth in the low UV wavelength range (DUV) at e.g. 193 nm, 248 nm or 365 nm. The penetration depth t is defined as the depth at which the incoming radiation has fallen to 1/e of its initial intensity.

Applied to FIG. 3, this knowledge means that the measuring radiation 42 in the visible wavelength range is already reflected on an outer individual layer of the coating 52. However, the EUV radiation 13 penetrates very deeply into the multilayer structure, a partial beam 55 being reflected on each individual layer 54. The effect of different penetration depths illustrated in FIG. 3 on the example of the mirror 16-6 occurs with the reflection on each of the mirrors 16-1 to 16-6 shown in FIG. 2.

With the qualifying method according to the invention in an evaluation device 46 the measurement results of the optical measurement measured for the different wavelengths, in the preceding exemplary embodiment the lateral image offset $\Delta x$, are now evaluated, taking into account the respective penetration depths of the radiation into the coating 52 for the different wavelengths used. Here the measured lateral image offset $\Delta x$ is compared with an anticipated image offset $\Delta x_0$. The anticipated image offset can be calculated, for example, using optical simulation programs upon the basis of the penetration depths t into the coatings 52 of the individual mirrors for the wavelengths used. Alternatively, the anticipated image offset can also be an image offset measured at an earlier time.

As a result of the evaluation, if appropriate, individual layers 54 of the mirror coatings 52 which have deformations can be identified. In which layer depths deformations of individual layers can be detected by the method according to the invention depends upon which wavelengths are used for the optical measurement. In the exemplary embodiment shown in FIG. 3, wherein the measuring radiation 42 has a visible wavelength, e.g. layer degradations at a layer depth of approximately 20 nm can be particularly well detected. The more wavelengths of different penetration depths are used for the optical measurement, the more accurately an existing layer degradation can be located.

According to one advantageous embodiment according to the invention the qualifying method is implemented at regular intervals of time, and any degradation occurring in the coating 53 depending on the layer depth is determined by comparing the measurement results.

Furthermore, as a result of the evaluation possible contamination of the surface of the mirror coatings 52 can be identified. If there is such contamination, the visible measuring radiation 42 would be absorbed by the latter to a considerable extent, whereas the EUV radiation 13 would experience less absorption. The EUV radiation 13 "sees" a surface effect and layer boundary surface degradation. On the other hand, the visible measuring radiation 42 only "sees" an effective medium, i.e. changes to the boundary surface coarseness are not detected. In connection with the small penetration depth the measurements of the visible measuring radiation 42 react sensitively to surface properties. In order to diagnose contamination, a comparison with threshold values is preferably made. The possibility according to the invention of detecting mirror contaminations enables identification and stopping of contamination sources in due time. Furthermore, cleaning can be initiated, as described in more detail below.

Often the last mirror element 16-6 in the optical path of the projection objective 16 is affected the most by contamination due to the vicinity to the wafer, in particular due to vapours from the layer of paint. With configurations where this is the case, the qualification apparatus according to FIG. 1 can be used to observe the surface cleanliness of the last mirror element 16-6. A contamination of the projection objective 16 determined during the evaluation could then be used as a measure for the contamination of the last mirror element 16-6. According to an alternative embodiment the measuring radiation 42 is only injected into the optical path of the projection objective before the last mirror element 16-6, and so only the last mirror element 16-6 is affected by the contamination measurement.

In one variant according to the invention of the embodiment according to FIG. 1 or the alternative embodiment only monitoring the last mirror element 16-6 a control unit 82 is connected downstream of the evaluation device 46 which either controls a cleaning apparatus 84 and/or an exchange apparatus 86 according to FIG. 1. The cleaning apparatus 84 is configured to clean the last mirror element 16-6 if contamination is discovered. This takes place, for example, by spraying atomic hydrogen 88 onto the reflection surface of the mirror element 16-6. The cleaning process can be efficiently arranged by monitoring using the qualifying apparatus according to the invention. Alternatively or in addition the control unit controls an exchange apparatus 86 which with corresponding contamination of the mirror element 16-6 replaces the latter with a replacement mirror element 16-6'. By monitoring the mirror element with the qualifying apparatus according to the invention during operation of the projection exposure tool, an operating time remaining until exchange is necessary can be reliably predicted, and a mirror exchange can be planned in advance.

Figure 5:
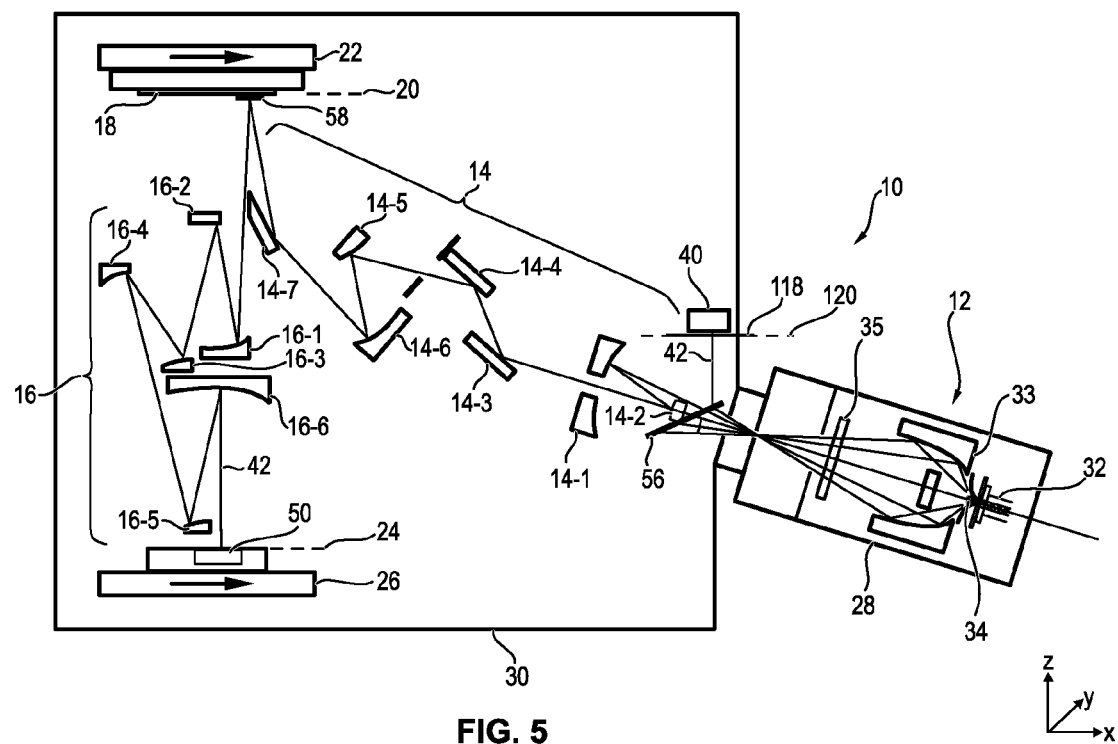
FIG. 5 the projection exposure tool according to FIG. 1 with an apparatus integrated into the latter for the combined qualification of the illumination system and projection optics.

FIG. 5 shows a further embodiment according to the invention of the qualifying apparatus with which layer degradations, not only in the projection objective 16, but also in the illumination system 14, can be detected. In this embodiment the qualifying apparatus comprises a folding mirror 56 which can be introduced into the optical path of the exposure radiation 13 in front of the first mirror element 14-1 of the illumination system 14 in order to take an optical measurement. A measuring mask 118 corresponding to the mask 18 of FIG. 2 is positioned above the folding mirror 56 in a plane 120 conjugate to the mask plane 20. The measuring radiation source 40 is positioned above the measuring mask 118 so that said radiation source radiates the measuring radiation 42 through the measuring mask 118.

In the mask plane 20 a mask 18 with a mirror surface 58 is arranged such that the measuring radiation 42 is reflected on the mirror surface 58. Alternatively, a structure-free mask can also be used as a mask 18. In the same way as for the measurement according to FIG. 2, in the embodiment according to FIG. 5 an optical measurement can be taken with two different wavelengths. For example, the lateral image location offset which occurs when a hole structure 21 is imaged into the substrate plane 24 with the measuring radiation 42 of at last two different wavelengths is measured. The different wavelengths can respectively be generated by the measuring radiation source 40. If one of the wavelengths is in the EUV range, according to the invention an EUV transmission reticle can be arranged as a measuring mask 118 in a plane of the illumination system 14 conjugate to the substrate plane 24. Particularly well suited for this application is, optionally, an optical design modified in comparison to the illumination system 14 shown in FIG. 5, with which a conjugate substrate plane is provided in front of the first mirror element 14-1, easily accessible to the measuring mask.

Figure 6:
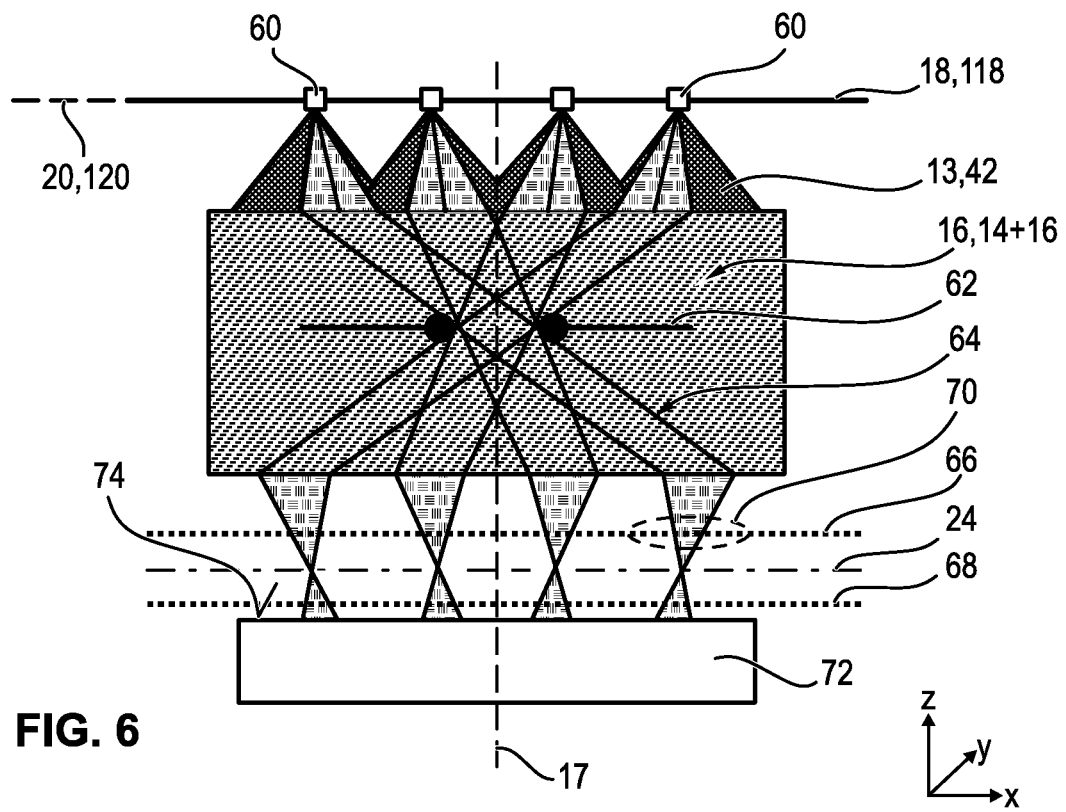
FIG. 6 a diagrammatic illustration of the apparatus according to the invention in an embodiment which is configured to take a pupil transmission measurement.

Alternatively or in addition to the image location offset measurement, with the qualifying apparatus according to FIG. 2 or according to FIG. 5 a pupil transmission measurement can also be taken with the respective wavelengths, as shown in FIG. 6. For this purpose the mask 18 in the mask plane 20 according to FIG. 1 or the mask 118 in the conjugate plane 120 according to FIG. 5 is provided with test structures 60 in the form of so-called pin holes distributed evenly over the mask surface which are punctiform in relation to the illumination wavelength. Alternatively, a mask basically permeable to radiation can also be used which is provided with punctiform test structures 60 impermeable to radiation. Depending on the embodiment, the optical system to be measured can be the projection objective 16 only or a combination of the illumination system 14 and the projection objective 16.

In order to generate a broad radiation cone for the radiation 13 and 42 passing from the test structures 60 the test structure 60 is preferably illuminated in over-irradiation. For this purpose the mask can be provided with a diffusion disc not shown in the drawing. The diffusion disc is generally irradiated with illumination radiation of comparably incoherent form (e.g. sigma of 0.8).

The course of the radiation 13 and 42 through the projection exposure tool 10 is as follows: The radiation radiated by the punctiform test structures 60 has a large angular distribution in relation to the optical axis 17 of the optical system 16 and 14+16, respectively. The bundle of rays 64 passing through the pupil 62 of the optical system only constitutes part of the radiation passing out of the test structures 60.

In order to measure the pupil transmission the sensor module, which in this case is only formed by a locally resolving detector 72, is disposed in a position displaced in relation to the substrate plane 24 in the z direction. Here the locally resolving detector 72 can either be arranged in a position e.g. displaced by 50 μm towards the optical system, and so intrafocal position 66, or e.g. displaced by 50 μm away from the optical system, and so extrafocal position 68. In these positions the test structures 60 generate light spots 70 which exceed the diameter of the test structure 60 in the substrate plane 24 by at least the factor 10. These light spots are also called pupillograms and constitute an image of the pupil illumination or the pupil transmission. With regard to the definition of a pupillogram reference is made to the article by Joe Kirk and Christopher Progler, "Pinholes and Pupil Fills", Microlithography World, Autumn 1997, pages 25-34. Using this type of pupil transmission measurement with radiation with different wavelengths one can identify in particular layer degradations which are established on mirrors of the optical system 16 and 14+16 close to the pupil.

Alternatively to the arrangement according to FIG. 6, for the pupil transmission measurement one can also dispense with the mask 18 or 118 or the latter can be designed to be totally transparent so that flood illumination is irradiated onto the optics to be measured. In this embodiment a mask with test structures distributed over the mask surface in the form of so-called pin holes is disposed in the substrate plane 24. The locally resolving detector is placed beneath the mask.

Figure 7:
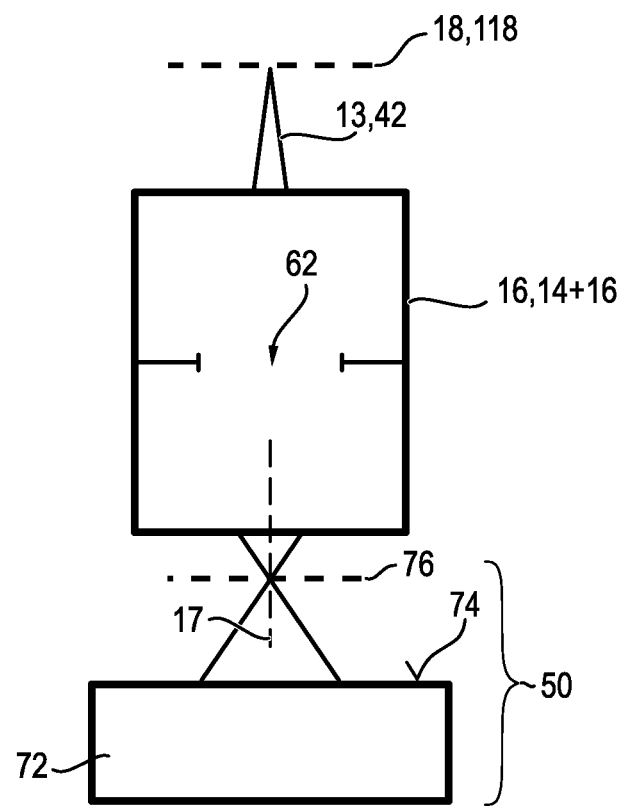
FIG. 7 a diagrammatic illustration of the apparatus according to the invention in a further embodiment which is configured to take a wavefront measurement, and for this purpose has a diffraction grating arrangement.

Alternatively or in addition to the image offset measurement and/or to the pupil transmission measurement, the optical measurement on the optical system 16 or 14+16, respectively, to be measured can also comprise a wavefront measurement, as illustrated in FIG. 7. For this purpose the mask 18 according to FIG. 2 or the measuring mask 118 according to FIG. 5 is in the form of a coherence mask, it being provided, for example, with one of the measuring patterns shown in U.S. Pat. No. 7,333,216 B2. The sensor module 50 is provided with a diffraction grating arrangement 76 which is disposed in the image plane or the substrate plane 24 of the projection objective 16. Moreover, the sensor module 50 comprises a locally resolving detector 72.

During the measurement the measuring pattern of the coherence mask is imaged onto the diffraction grating arrangement 76. By superposition of the waves generated by diffraction a pattern is produced on a detection surface 74 of the locally resolving detector 72 in the form of an interferogram. The diffraction grating arrangement 76 is moved laterally to the optical axis 17, and a number of interferograms produced in this way are detected using the detector 72. With an evaluation device the wavefront of the radiation 13 and 42 after passing through the optical system 16 or 14+16 is measured from the interferograms recorded, and from this a deviation of the measured wavefront from an anticipated desired wavefront is determined.

The measurement taken here is a measurement by shearing interferometry, the functional principle of which is known to the person skilled in the art, for example from U.S. Pat. No. 7,333,216 B2, and so will not be enlarged upon at this point. As described in this publication, for the interferometric measurement reference radiation can optionally also be decoupled from the radiation wave and be delivered to the sensor module 50. In the measuring arrangement according to FIG. 7 only one measuring channel is shown. Alternatively, a number of measuring channels can also be provided so that a parallel measurement is possible at the same time at a number of field points.

Figure 8:
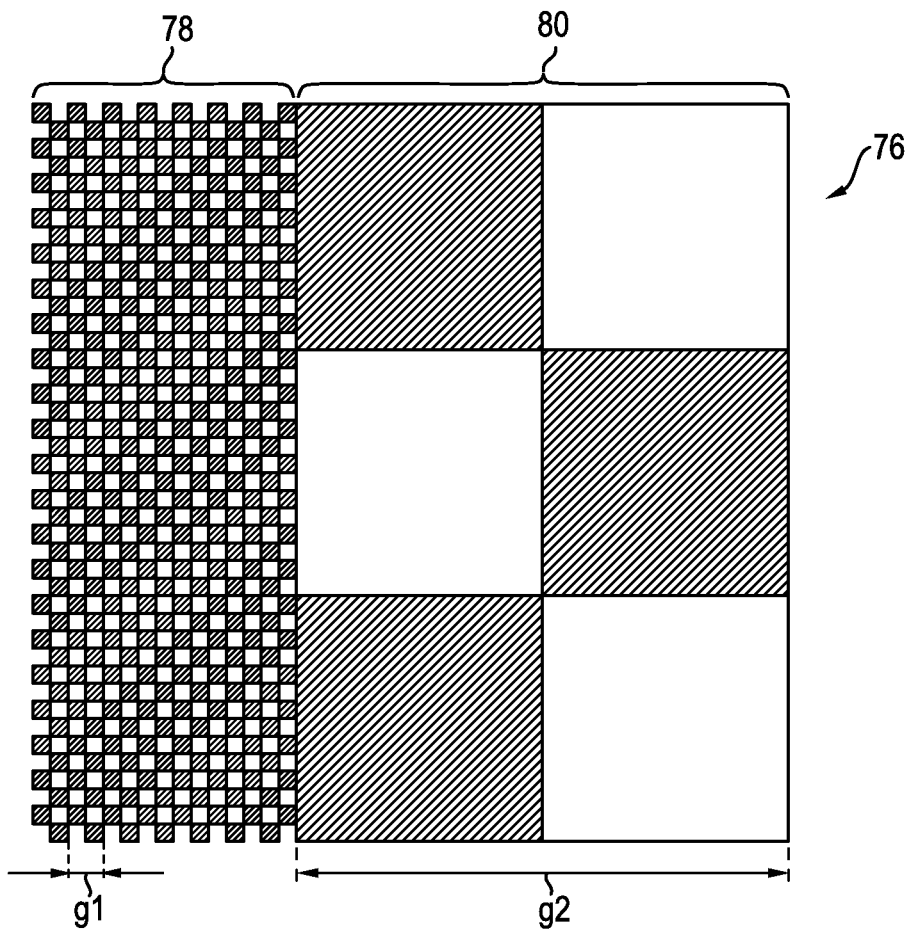
FIG. 8 a top view of a section of an embodiment of the diffraction grating arrangement of the apparatus according to FIG. 7, and FIG. 9 a diagrammatic sectional view of a last mirror element of a projection element with an interferometer arrangement for observing the surface cleanliness of the last mirror element and a cleaning apparatus for cleaning the latter.

FIG. 8 shows a top view onto the diffraction grating arrangement 76 in an embodiment according to the invention. The diffraction grating arrangement shown has a first diffraction grating 78 with a first grating constant $g_1$ and a second diffraction grating 80 with a grating constant $g_2$. The grating constant $g_1$ of the first diffraction grating 78 is configured to diffract the EUV exposure radiation 13, whereas the grating constant $g_2$ of the second diffraction grating 80 in the example shown is configured to diffract measuring radiation 42 with a wavelength of 193 nm. Therefore the grating constant $g_2$ is greater than the grating constant $g_1$ by more than one order of magnitude. The locally resolving detector 72 is configured to detect both wavelengths used during the measurement, in the present case EUV and 193 nm.

Moreover, a spectrometric measurement can also be taken on the optical system 16 and 14+16 with different wavelengths. With this type of measurement, upon the basis of vibrational excitation one can draw a conclusion with regard to the type of contamination, layer depth resolved upon the basis of the use according to the invention of different wavelengths.

If layer degradation is now determined from the comparison of the measurements of different wavelengths, by comparing the results obtained using the different optical measuring methods described above, in particular the pupil transmission measurements and the wavefront measurements, the layer degradation occurring can be assigned to one or more of the mirrors 14-1 to 14-7 or 16-1 to 16-6. For this purpose, in particular an analysis of the optical path using ray tracing is implemented. Preferably, through ray tracing, the position of a layer degradation on the surface of a corresponding mirror element is also determined.

Figure 9:
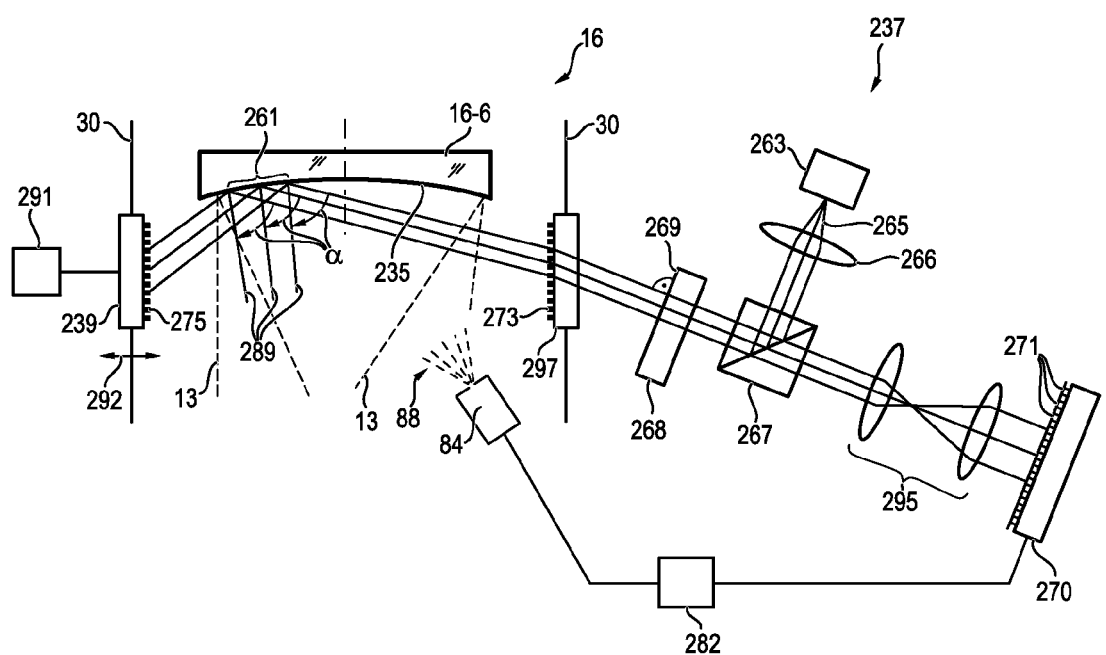

FIG. 9 illustrates an interferometer arrangement 237 which can be used as an alternative or in addition to the qualification apparatus described above for observing the last mirror element 16-6 of the projection objective 16 according to FIG. 1. The interferometer arrangement 237 comprises a radiation source 263 for generating measuring radiation 265. The radiation source 263 here can be, for example, a helium neon laser which emits the measuring radiation 265 with a wavelength of 632.8. The measuring radiation 265 is collimated by diagrammatically illustrated collimating optics 266 and is reflected on a beam splitter 267. It then passes through a wedge plate 268 with a partially reflective surface 269 oriented orthogonally to the beam direction of the measuring radiation 265 passing through the wedge plate 268, which forms a Fizeau surface of the interferometer arrangement 237.

Measuring radiation reflected on the Fizeau surface 269 is used as reference radiation, passes through the beam splitter 267 in a straight line, and is projected by camera optics 295 onto a two-dimensionally locally resolving radiation detector 270. The radiation detector 270 can be a CCD detector which has a plurality of pixels 271 arranged in a two-dimensional pattern. Part of the measuring radiation 265 passing through the Fizeau surface 269 passes through a window 297 which is fitted in a housing 30 of the EUV projection objective 16, into an interior of the housing 30. In the interior of the housing 30 a vacuum, for example, can be provided, or a gas atmosphere of an appropriate gas, which has little interaction with the exposure radiation 13.

There are provided on an inner surface of the window 297 beam-forming optics in the form of a computer-generated hologram (CGH) 273 which is formed such that the measuring radiation collimated as a parallel beam and striking the CGH 273 is diffracted by the CGH 273, for example in a first diffraction order, and is expanded here so that the measuring radiation strikes an expanded region 261 of the reflective surface 235 of the last mirror element 16-6. From here the measuring radiation is reflected and strikes in turn, as an expanded bundle of rays, a further CGH 275 of the back-reflector 239 which is configured such that the measuring radiation striking the CGH 275 is reflected back as accurately as possible into itself. Therefore, for the radiation which is reflected on the CGH 275 below a given diffraction order, for example the first diffraction order, the CGH 275 performs the function of a back-reflector.

The back-reflected measuring radiation then in turn strikes an expanded region of the optical surface 235 of the mirror element 16-6. Provided the condition of accurate back-reflection is fulfilled, this expanded region will coincide with the expanded region 261 which the measuring radiation coming from the CGH 273 strikes. The measuring radiation from the CGH 275 striking the region 61 is in turn reflected on the optical surface 235 and strikes the CGH 273, and is formed by the latter into a substantially parallel measuring radiation beam which passes through the Fizeau surface 269 and the wedge plate 268, then passes through the beam splitter 267, and is projected by the camera optics 295 onto the detector 270 so that an interference pattern is produced on the detector 270 due to the interference producing superposition of the reference radiation reflected on the Fizeau surface 269 with the measuring radiation, which has interacted twice with the surface 235 of the mirror element 16-6 in the region 261. This is inputted into a control unit 282 by the detector 270.

The overall structure comprising the components of the interferometer arrangement 237 and the mirror element 16-6 is accessible to the numerical simulation, and so with a known geometry of the components the interference pattern produced can be calculated by methods such as, for example, ray tracing. By comparing a measured interference pattern with the calculated interference pattern it is then possible with appropriate calibration of the components of the interferometer arrangement 237 to conclude that there are deviations of a surface form of the optical surface 235 in the region 261 from a desired form, and so that there are contaminations on the optical surface 235.

Even if an interference pattern produced can not be predicted accurately by numerical calculations, it is nevertheless possible to detect changes to the interference pattern dependently upon time. From these changes it is then possible to draw conclusions with regard to changes to the form of the optical surface 235 in the region 261. For example, it is possible to establish here whether a radius of curvature of the surface 235 increases or decreases over time in the region 261.

FIG. 9 shows another actuator 291 which is configured to displace the CGH 275 in a direction indicated in FIG. 9 by an arrow 292 in order to generate a phase shift of the measuring radiation thrown back on the CGH 275, and so to generate a phase shift in the interference pattern detected by the detector 270. It is therefore possible to utilise the principles of phase shifting interferometry (PSI), and for a measurement of the optical surface 235 in the region 261 to detect a number of interferograms with the detector 270 with respectively different positions of the CGH 275. An evaluation of the number of interferograms is advantageous with regard to accuracy and clarity of the measurement taken. Background information on phase shifted interferometry can be taken from Chapter 14 of the text book by Daniel Malacara, Optical Shop Testing, 2nd edition, Wiley Interscience Publication (1992).

In FIG. 9 three surface normals 289 established at different positions of the region 261 are drawn in. Furthermore, in FIG. 9 three angles of incidence (a) of partial beams of the measuring beam bundle are drawn in which strike the region 261. Due to the curvature of the surface 235 and the divergence of the striking measuring radiation the angles of incidence are not equal at every position of the region 261. However, it is possible to average the angles of incidence over the surface of the region 261 so as to thus determine an average angle of incidence of the measuring radiation over the surface 235. It is also clear from the diagrammatic illustration of FIG. 9 that the measuring radiation strikes the surface 235 at a relatively large angle of incidence. This angle of incidence is in particular larger than 30°.

If increased contamination of the surface 235 is observed by the interferometer arrangement 237, via the control unit 82 already described with regard to FIG. 1 the cleaning apparatus 84 is activated to spray atomic hydrogen 88 onto the surface 235, and so to clean the latter. Furthermore, the control unit according to FIG. 9 can also control an exchange device 86 according to FIG. 1 in order to replace the mirror element 16-6 with a replacement mirror element 16-6' if there is corresponding contamination of said mirror element 16-6. The basic principle of the interferometer arrangement 237 according to FIG. 9 is known to the person skilled in the art from DE 10 2005 056 914 A1. Alternatively the interferometer arrangement can also be used according to the invention in other embodiments described in DE 10 2005 056 914 A1. These embodiments are herewith explicitly incorporated into the disclosure of this application.

The above description of various embodiments has been given by way of example. From the disclosure given, those skilled in the art will not only understand the present invention and its attendant advantages, but will also find apparent various changes and modifications to the structures and methods disclosed. It is sought, therefore, to cover all such changes and modifications as fall within the spirit and scope of the invention, as defined by the appended claims, and equivalents thereof.

The invention claimed is:

1. An apparatus for an interferometric wavefront measurement on optics of a projection exposure tool for microlithography, comprising:
   a diffraction grating arrangement comprising at least two diffraction gratings with mutually differing grating periods, the grating periods being adapted to diffract electromagnetic radiation of respective, mutually differing wavelengths, a coherence mask comprising a measuring pattern arranged such that the measuring pattern is imaged by the optics onto the diffraction grating arrangement, and a locally resolving detector configured to detect the electromagnetic radiation of the respective, mutually differing wavelengths in order to record interferograms generated by diffraction at the diffraction gratings.

2. The sensor module according to claim 1, wherein one of the diffraction gratings is configured to diffract extreme-ultraviolet radiation, and a second of the diffraction gratings is configured to diffract radiation with a wavelength of greater than 100 nm.

3. The apparatus of claim 1, wherein the locally resolving detector is further configured to output results of a measurement comprising at least one of a lateral offset between a detected image of a first of the wavelengths and a detected image of a second of the wavelengths, a difference between a pupil transmission for the first of the wavelengths and the second of the wavelengths, or a difference in an interferometric wavefront between the first of the wavelengths and the second of the wavelengths, and further comprising an evaluation device comprising a processor programmed to evaluate a degradation of a layer of at least one mirror in an optical path of the respective, mutually differing wavelengths based on the results of the measurement and respective penetration depths for each of the first and second wavelengths into a coating of the at least one mirror.

4. The apparatus of claim 3, wherein the at least one mirror is one of a plurality of mirrors arranged in an optical path of the first wavelength and the further wavelength, and wherein the processor of the evaluation device is further programmed to determine the at least one mirror from the plurality of mirrors according to the interferometric wavefront measurement and the respective penetration depths of the radiation into the coating of the mirror for each of the different wavelengths.

5. An apparatus for qualifying optics of a projection exposure tool for microlithography, the optics comprising at least one mirror element with a reflective coating, the apparatus comprising:

a measuring radiation source configured to generate electromagnetic radiation of at least one first wavelength different from an exposure wavelength of the projection exposure tool, a test structure arranged in a beam path of the electromagnetic radiation generated by the measuring radiation source such that the test structure is imaged into a substrate plane by the optics of the projection exposure tool, a measuring device configured to take an optical measurement on the optics with the electromagnetic radiation of the first wavelength and with a further wavelength, and an evaluation device comprising a processor programmed to evaluate results of the measurement of the measuring device for the first and the further wavelengths based on respective penetration depths of the radiation into the coating of the mirror element for each of the first and the further wavelengths.

6. The apparatus according to claim 5, wherein the measuring device comprises:

a sensor module for an interferometric wavefront measurement on the optics of the projection exposure tool, the sensor module comprising:

a locally resolving detector arranged in the substrate plane and configured to detect electromagnetic radiation of at least two different wavelengths, and at least two diffraction gratings with different grating periods, the respective grating periods of each of the diffraction gratings being adapted to diffract the electromagnetic radiation of respectively one of the two different wavelengths.

7. A projection exposure tool for microlithography comprising an apparatus according to claim 5, which is configured to image an object structure with exposure radiation onto a substrate, the electromagnetic radiation with the further wavelength being the exposure radiation.

8. The projection exposure tool according to claim 7, which is configured for operation with extreme ultraviolet (EUV) radiation.

9. The apparatus of claim 5, wherein the measuring device is further configured to take an optical measurement of the image of the test structure.

10. The apparatus of claim 5, wherein the optical measurement comprises at least one of a lateral offset for an image as produced by the first wavelength and the image as produced by the further wavelength in a substrate plane of the projection exposure tool, a pupil transmission measurement for the first wavelength and the further wavelength, or an interferometric wavefront measurement on the optics of the projection exposure tool for the first wavelength and the further wavelength, and wherein the processor of the evaluation device is further programmed to determine a degradation of a layer of the at least one mirror element.

11. The apparatus of claim 10, wherein the at least one mirror element is one of a plurality of mirrors arranged in an optical path of the first wavelength and the further wavelength, and wherein the processor of the evaluation device is further programmed to determine the at least one mirror element from the plurality of mirrors according to the pupil transmission measurement and the respective penetration depths of the radiation into the coating of the mirror element for the first and the further wavelengths.

* * * * *

UNITED STATES PATENT AND TRADEMARK OFFICE
CERTIFICATE OF CORRECTION

| | | |
|---|---|---|
| PATENT NO. | : 8,908,192 B2 | Page 1 of 1 |
| APPLICATION NO. | : 13/754446 | |
| DATED | : December 9, 2014 | |
| INVENTOR(S) | : Markus Goeppert | |

It is certified that error appears in the above-identified patent and that said Letters Patent is hereby corrected as shown below:

In the Specification:
Column 14, Line 21; change "(a)" to -- ($\alpha$) --.

In the Claims:
Column 15, Line 8; In Claim 2 change "sensor module" to -- apparatus --.

Signed and Sealed this
Seventeenth Day of November, 2015

Michelle K. Lee
*Director of the United States Patent and Trademark Office*